United States Patent
Hara et al.

(10) Patent No.: US 11,033,464 B2
(45) Date of Patent: Jun. 15, 2021

(54) COMPOSITION WITH EXCELLENT STORAGE STABILITY USING HIGHLY BASIC FILLER

(71) Applicant: SHOFU INC., Kyoto (JP)

(72) Inventors: Daisuke Hara, Kyoto (JP); Naoya Kitada, Kyoto (JP); Toshiyuki Nakatsuka, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 16/205,396

(22) Filed: Nov. 30, 2018

(65) Prior Publication Data

US 2019/0262238 A1  Aug. 29, 2019

(30) Foreign Application Priority Data

Dec. 1, 2017 (JP) .............................. JP2017-231353

(51) Int. Cl.
| | |
|---|---|
| A61K 6/30 | (2020.01) |
| A61K 6/16 | (2020.01) |
| A61K 6/62 | (2020.01) |
| A61K 6/76 | (2020.01) |
| A61K 6/77 | (2020.01) |
| A61K 6/79 | (2020.01) |
| A61K 6/884 | (2020.01) |
| A61K 6/887 | (2020.01) |

(52) U.S. Cl.
CPC ............... *A61K 6/30* (2020.01); *A61K 6/16* (2020.01); *A61K 6/62* (2020.01); *A61K 6/76* (2020.01); *A61K 6/77* (2020.01); *A61K 6/79* (2020.01); *A61K 6/884* (2020.01); *A61K 6/887* (2020.01)

(58) Field of Classification Search
CPC .................................................... A61K 6/887
See application file for complete search history.

(56) References Cited

U.S. PATENT DOCUMENTS

| | | |
|---|---|---|
| 2007/0100019 A1 | 5/2007 | Sun |
| 2007/0203257 A1* | 8/2007 | Qian .................. A61K 6/887 |
| | | 523/116 |
| 2010/0010115 A1* | 1/2010 | Kohro .................. C09J 143/02 |
| | | 523/116 |
| 2010/0240795 A1 | 9/2010 | Burtscher et al. |
| 2010/0240797 A1 | 9/2010 | Yarimizu et al. |
| 2012/0059083 A1 | 3/2012 | Tokui et al. |

FOREIGN PATENT DOCUMENTS

| | | |
|---|---|---|
| JP | 2008-273890 | 11/2008 |
| JP | 2009-503086 | 1/2009 |
| JP | 2009-292761 | 12/2009 |
| JP | 2010-215824 | 9/2010 |
| JP | 2010-222354 | 10/2010 |
| JP | 2011-016775 | 1/2011 |
| JP | 2012-051856 | 3/2012 |
| JP | 2014-152106 | 8/2014 |
| JP | 2016-113438 | 6/2016 |
| JP | 2016-124811 | 7/2016 |

OTHER PUBLICATIONS

English machine translation of Kashiki et al. (JP 2016-113438) (Year: 2016).*
Notification of Reasons for Refusal dated Jun. 7, 2018 in corresponding Japanese Patent Application No. 2017-231353, English Translation.
Extended European Search Report dated Sep. 4, 2019 in corresponding European Patent Application No. 18209376.5.

* cited by examiner

*Primary Examiner* — Michael F Pepitone
(74) *Attorney, Agent, or Firm* — Wenderoth, Lind & Ponack, L.L.P.

(57) ABSTRACT

To provides a polymerizable composition having high storage stability and high color stability. To provide a two-paste type dental polymerizable composition of the present invention is a two-paste type dental polymerizable composition comprising a first paste containing (A) at least one kind of polemerizable monomer, an (B) organic peroxide as a chemical polymerization initiator, and a (C) basic filler, and a second paste containing (A) at least one kind of polemerizable monomer, a (C) basic filler and an (D) aromatic amine compound as a chemical polymerization accelerator, wherein the second paste contains 30 to 80 parts by weight of the (C) basic filler based on 100 parts by weight of the total amount of the second paste.

7 Claims, No Drawings

COMPOSITION WITH EXCELLENT STORAGE STABILITY USING HIGHLY BASIC FILLER

CROSS-REFERENCE TO RELATED APPLICATIONS

This application is based on and claims the benefit of priority from Japanese Patent Application Serial No. 2017-231353 (filed on Dec. 1, 2017), the contents of which are hereby incorporated by reference in their entirety.

BACKGROUND OF THE INVENTION

Field of the Invention

The present invention relates to a two-paste type dental polymerizable composition.

Description of the Related Art

In the dental field, a polymerizable composition containing a polymerizable monomer, a chemical polymerization initiator and a chemical polymerization accelerator has been widely used as a dental resin cement, a dental abutment construction material, a dental adhesive material, a dental coating material, a pit and fissure plugging material, a composite resin, a dental autopolymerizing resin, a dental pretreatment material, a denture base material and the like.

A two-paste type dental polymerizable composition is a material which can be used to restore an anatomical form of a carious part or a dental defect. Properties suitable for the desired use, for example, the mechanical strength and the adhesive strength capable of withstanding the occlusal pressure, and the color tone close to that of a tooth substance and the like can be obtained by curing a dental polymerizable composition by a polymerization reaction. The polymerization reaction of the polymerizable composition is roughly classified into a photopolymerization in which polymerization is initiated by light irradiation, and a chemical polymerization in which polymerization is initiated by a chemical polymerization initiator and a chemical polymerization accelerator. Although the photopolymerization can be performed at an arbitrary time of the operator by light irradiation, the part to which light does not reach cannot be polymerized at all by the photopolymerization. On the other hand, although the curing time in the chemical polymerization depends on the type and amount of both of the chemical polymerization initiator and the chemical polymerization accelerator and the like, because the part to which light does not reach can be polymerized, therefore, the chemical polymerization has been used for many dental materials. In addition, dental materials are required to have high storage stability in which a decrease in hardenability and a change in properties are not found regardless of the use thereof, and high color tone stability in which color tone does not change after application to the oral cavity.

In a polymerizable composition in which the polymerization reaction is the chemical polymerization, it is required that the components of the polymerizable composition are divided into at least two packages are stored so as not to contact the chemical polymerization initiator and the chemical polymerization accelerator with microcapsules or the like. In addition, the chemical polymerization reaction is initiated by contacting the chemical polymerization initiator and the chemical polymerization accelerator by performing operations such as mixing and kneading of the components divided into each package at the time of use.

In the dental polymerizable composition, an oxidation reduction (redox) reaction by a chemical polymerization initiator (oxidizing material) and a chemical polymerization accelerator (reducing material) is generally used as a chemical polymerization reaction, and free radicals generated by the oxidation reduction reaction serve as a base of the polymerization reaction.

Specifically, benzoyl peroxide and aromatic amine compounds have been widely used as a chemical polymerization initiator and a chemical polymerization accelerator. The chemical polymerization initiator system comprising benzoyl peroxide and aromatic amine compound has high polymerization activity and thus exhibits high mechanical properties and sharp curability. However, there are problems in the above-mentioned chemical polymerization initiator system that the storage stability decreases due to the deactivation of the chemical polymerization initiator and/or the chemical polymerization accelerator with time, and the color tone stability is low due to the change of the remaining aromatic amine which does not contribute to the polymerization reaction to a colorant substance.

As a composition having improved the storage stability and color tone stability, a chemical polymerization initiator system in which a hydroperoxide having higher thermal stability as a chemical polymerization initiator is combined with thiourea as a chemical polymerization accelerator has been proposed (Japanese Unexamined Patent Application Publication No. 2009-292761 and Japanese Unexamined Patent Application Publication (Translation of PCT Application) No. 2009-503086). The chemical polymerization initiator system combining a hydroperoxide and a thiourea compound is excellent in the color tone stability after polymerization, however, there has been a problem that the reactivity is poor due to high stability of the hydroperoxide and therefore the mechanical strength is low.

In order to accelerate the curing rate of the above-mentioned chemical polymerization initiator system, a technique of compounding a compound of copper which is a transition metal as a further chemical polymerization accelerator (Japanese Unexamined Patent Application Publication No. 2010-215824) and a technique of compounding a compound of vanadium which is a transition metal as a further chemical polymerization accelerator (Japanese Unexamined Patent Application Publication No. 2012-51856 and Japanese Unexamined Patent Application Publication No. 2014-152106) has been proposed. However, since the transition metal exhibits a color tone corresponding to the valence thereof, there is a possibility that an unexpected color tone is exhibited during the storage period due to fluctuations in (oxidation reduction) potential or pH in the composition. Furthermore, the metal compound and the vanadium compound are poorly soluble or insoluble in the polymerizable monomer, and exist in a nonuniform state in the composition. Therefore, there has been a problem that the reaction efficiency of the chemical polymerization initiator and the chemical polymerization accelerator is lower than that in the dissolved state.

SUMMARY OF THE INVENTION

Technical Problem

The present invention provides a polymerizable composition having high storage stability and high color tone stability in order to solve the above conventional problems.

As a result of intensive investigations, it has been found that the color tone stability after polymerization is improved as an unexpected effect in addition to that the coexistence of a specific basic filler and a specific aromatic amine compound which is a chemical polymerization accelerator can suppress the deactivation of the aromatic amine compound to improve the storage stability, and the present invention has been completed.

The reason why the storage stability and the color tone stability are improved is presumed to be as follows. Since the aromatic amine compound is basic and becomes stable in the presence of a filler having a higher basicity, it is presumed that the deactivation can be suppressed to lead an improvement in the storage stability. Furthermore, it is considered that since basic condition is maintained even after polymerization, the remaining aromatic amine compound that does not contribute to the reaction is stable, and thus it is difficult to change to a colorant substance to improve the color tone stability.

Solution to Problem

The two-paste type dental polymerizable composition of the present invention is a two-paste type dental polymerizable composition comprising a first paste containing (A) at least one kind of polemerizable monomer, an (B) organic peroxide as a chemical polymerization initiator, and a (C) basic filler, and a second paste containing (A) at least one kind of polemerizable monomer, a (C) basic filler and an (D) aromatic amine compound as a chemical polymerization accelerator, wherein the second paste contains 30 to 80 parts by weight of the (C) basic filler based on 100 parts by weight of the total amount of the second paste.

In the two-paste type dental polymerizable composition of the present invention, it is preferable that a dispersion of 1.0 g of the (C) basic filler in a mixed solution of 40 g of distilled water and 10 g of ethanol has pH-value in the range from 7.5 to 9.0 after stirring for 1 hour.

In the two-paste type dental polymerizable composition of the present invention, it is preferable that the total compounding amount of the (C) basic filler contained in the first paste and the second paste is in the range from 40 to 80 parts by weight based on 100 parts by weight of the total composition of the first paste and the second paste.

In the two-paste type dental polymerizable composition of the present invention, it is preferable that the first paste and the second paste contain substantially no water.

In the two-paste type dental polymerizable composition of the present invention, it is preferable that the first paste and the second paste contain substantially no acidic group-containing compound.

In the two-paste type dental polymerizable composition of the present invention, it is preferable that a volume mixing ratio of the first paste to the second paste is in the range from 1:0.9 to 0.9:1.

It is preferable that the compounding amount of the (A) at least one kind of polemerizable monomer contained in the first paste is within a range from 20 to 40 parts by weight based on 100 parts by weight of the total amount of the composition of the first paste.

It is preferable that the compounding amount of the (B) organic peroxide as a chemical polymerization initiator contained in the first paste is within a range from 0.1 to 5 parts by weight based on 100 parts by weight of the total amount of the (A) at least one kind of polemerizable monomer in the first paste.

It is preferable that the compounding amount of the (C) basic filler contained in the first paste is within a range from 10 to 80 parts by weight based on 100 parts by weight of the total amount of the composition of the first paste.

It is preferable that the compounding amount of the (A) at least one kind of polemerizable monomer contained in the second paste is within a range from 20 to 40 parts by weight based on 100 parts by weight of the total amount of the composition of the second paste.

It is preferable that the compounding amount of the (C) basic filler contained in the second paste is within a range from 30 to 80 parts by weight based on 100 parts by weight of the total amount of the composition of the second paste.

It is preferable that the compounding amount of the (D) aromatic amine compound as a chemical polymerization accelerator contained in the second paste is within a range from 0.1 to 5 parts by weight based on 100 parts by weight of the total amount of the polemerizable monomer in the second paste.

It is preferable that the total amount of the (C) basic filler in the first paste and the second paste is preferably within a range from 40 to 80 parts by weight based on 100 parts by weight total amount of the composition in which the first paste and the second paste are combined.

Advantageous Effects of Invention

The present invention provides a polymerizable composition having high storage stability and high color stability.

DETAILED DESCRIPTION OF THE PREFERRED EMBODIMENTS

The present invention will be described in detail below. As a (A) polemerizable monomer constituting the two-paste type dental polymerizable composition of the present invention, known polemerizable monomer can be used without any limitation as long as the polemerizable monomer has one or more polymerizable groups. A polymerizable monomer in which the polymerizable group exhibits radical polymerizability is preferable. Specifically, from the viewpoint of easy radical polymerization, (meth) acrylic group and/or (meth) acrylamide group is preferable as the polymerizable group. In the present specification, "(meth) acrylic" means acrylic and/or methacrylic, "(meth) acryloyl" means acryloyl and/or methacryloyl, and, "(meth) acrylate" means acrylate and/or methacrylate.

Specific examples of a polemerizable monomer having one radical polymerizable group include 2-hydroxyethyl (meth) acrylate, 3-hydroxypropyl (meth) acrylate, 4-hydroxybutyl (meth) acrylate, 6-hydroxyhexyl (meth) acrylate, 10-hydroxydecyl (meth) acrylate, propylene glycol mono (meth) acrylate, glycerol mono (meth) acrylate, erythritol mono (meth) acrylate, N-methylol (meth) acrylamide, N-hydroxyethyl (meth) acrylamide, N,N-(dihydroxyethyl) (meth) acrylamide, methyl (meth) acrylate, ethyl (meth) acrylate, propyl (meth) acrylate, isopropyl (meth) acrylate, butyl (meth) acrylate, isobutyl (meth) acrylate, benzyl (meth) acrylate, lauryl (meth) acrylate, 2,3-dibromopropyl (meth) acrylate, 3-(meth) acryloyloxypropyl trimethoxysilane, 11-(meth) acryloyloxyundecyl trimethoxysilane, (meth) acrylamide and the like. Among these, from the viewpoint of high affinity of the polymerizable composition with the tooth material to be obtained, 2-hydroxyethyl (meth) acrylate, 3-hydroxypropyl (meth) acrylate, glycerol mono (meth) acrylate and erythritol mono (meth) acrylate are preferable.

Specific Examples of the polymerizable monomer having two radical polymerizable groups include 2,2-bis ((meth) acryloyloxy phenyl) propane, 2,2-bis [4-(3-(meth) acryloyloxy)-2-hydroxy propoxyphenyl] propane (generally called "Bis-GMA"), 2,2-bis (4-(meth) acryloyloxy phenyl) propane, 2,2-bis (4-(meth) acryloyloxy polyethoxyphenyl) propane, 2,2-bis (4-(meth) acryloyloxy diethoxyphenyl) propane), 2,2-bis (4-(meth) acryloyloxy tetraethoxyphenyl) propane, 2,2-bis (4-(meth)) acryloyloxy pentaethoxyphenyl) propane, 2,2-bis (4-(meth) acryloyloxy dipropoxypheny) propane, 2-(4-(meth) acryloyloxy diethoxyphenyl)-2-(4-(meth) acryloyloxy diethoxyphenyl) propane, 2-(4-(meth) acryloyloxy diethoxyphenyl)-2-(4-(meth) acryloyloxy triethoxyphenyl) propane, 2-(4-(meth) acryloyloxy dipropoxyphenyl)-2-(4-(meth) acryloyloxy triethoxyphenyl) propane, 2,2-bis (4-(meth) acryloyloxy propoxyphenyl) propane, 2,2-bis (4-(meth) acryloyloxy isopropoxyphenyl) propane, 1,4-bis (2-(meth) acryloyloxyethyl) pyromellitate, glycerol di (meth) acrylate, ethyleneglycol di (meth) acrylate, diethyleneglycol di (meth) acrylate, triethylene glycol di (meth) acrylate, propylene glycol di (meth) acrylate, butylene glycol di (meth) acrylate, neopentyl glycol di (meth) acrylate, polyethylene glycol di (meth) acrylate, 1,3-butanediol di (meth) acrylate, 1,5-pentanediol di (meth) acrylate, 1,6-hexanediol di (meth) acrylate, 1,10-decanediol di (meth) acrylate, 1,2-bis (3-methacryloyloxy-2-hydroxypropoxy) ethane, 2,2,4-trimethyl hexamethylene bis (2-carbamoyloxy ethyl) dimethacrylate (generally called "UDMA"), 1,2-bis (3-methacryloyloxy-2-hydroxy propoxy) ethane and the like. Among these, from the viewpoint of mechanical strength, 2,2-bis [4-(3-(meth) acryloyloxy)-2-hydroxy propoxyphenyl] propane, 2,2-bis (4-(meth) acryloyloxy polyethoxyphenyl) propane, and 1,6-bis (methacrylethyl oxycarbonylamino)-2,2,4,-trimethylhexane are preferable, and from the viewpoint of handling, triethylene glycol di (meth) acrylate, neopentyl glycol di (meth) acrylate and glycerol di (meth) acrylate are preferable. Among the 2,2-bis (4-(meth) acryloyloxy polyethoxyphenyl) propanes, a compound having an average addittion mole number of ethoxy group of 2.6 (generally called "D2.6E") is preferable.

Specific Examples of the polymerizable monomer having three or more radical polymerizable groups include trimethylolpropane tri (meth) acrylate, trimethylolethane tri (meth) acrylate, trimethylolmethane tri (meth) acrylate, pentaerythritol tri (meth) acrylate, pentaerythritol tetra (meth) acrylate, dipentaerythritol penta (meth) acrylate, N,N-(2,2,4-trimethylhexamethylene) bis [2-(aminocarboxy) propane-1,3-diol] tetra methacrylate, 1,7-diacryloyloxy-2,2,6,6-tetra acryloyloxymethyl-4-oxyheptane and the like. Among these, trimethylolpropane tri (meth) acrylate is preferable in that the mechanical strength of the resulting polymerizable composition is large.

As the polymerizable monomer used in the two-paste type dental polymerizable composition of the present invention, not only the above-mentioned polymerizable monomer may be used alone, but also two or more kinds of organic peroxides may be used in combination. From the viewpoint of improving mechanical properties, the compounding amount of the polymerizable monomer having two radical polymerizable groups is preferably set to 40 parts by weight or more, more preferably 60 parts by weight or more based on 100 parts by weight of the total amount of polymerizable monomer in the two-paste type dental polymerizable composition. When the compounding amount of the polymerizable monomer having two radical polymerizable groups is less than 40 parts by weight, there is a case in which mechanical properties may be lowered.

Specific examples of the (B) organic peroxide as a chemical polymerization initiator include diacyl peroxides, peroxy esters, dialkyl peroxides, peroxy ketals, ketone peroxides and hydro peroxides. Specific examples of diacyl peroxides include benzoyl peroxide, 2,4-dichlorobenzoyl peroxide, m-toluoyl peroxide and the like. Specific examples of peroxy esters include t-butyl peroxy benzoate, bis-t-butyl peroxy isophthalate, 2,5-dimethyl-2,5-bis (benzoyl peroxy) hexane, t-butyl peroxy-2-ethyl hexanoate, t-butylperoxy isopropyl carbonate and the like. Specific examples of dialkyl peroxides include dicumyl peroxide, di-t-butyl peroxide, lauroyl peroxide and the like. Specific examples of peroxyketals include 1,1-bis (t-butyl peroxy)-3,3,5-trimethyl cyclohexane, 1,1-bis (t-butyl peroxy) cyclohexane, 1,1-bis (t-hexyl peroxy) cyclohexane and the like. Specific examples of ketone peroxides include methyl ethyl ketone peroxide, cyclohexanone peroxide, methyl acetoacetate peroxide and the like. Specific examples of hydro peroxides include t-butyl hydro peroxide, cumene hydro peroxide, p-diisopropyl benzene peroxide, 1,1,3,3-tetramethyl butyl hydro peroxide and the like. Among these organic peroxides, benzoyl peroxide and cumene hydroperoxide are preferable from the viewpoint of curability. The compounding amount of the (B) organic peroxide as a chemical polymerization initiator is preferably set to 0.1 to 5 parts by weight, more preferably set to 0.3 to 3 parts by weight based on 100 parts by weight of the total amount of polymerizable monomer in the first paste from the viewpoint of improving the curability. When the compounding amount of the organic peroxide is more than 5 parts by weight, it may be difficult to ensure sufficient operation time. When the compounding amount of the organic peroxide is less than 0.1 parts by weight, there is a case in which mechanical strength may be insufficient.

As the organic peroxide, the above-mentioned organic peroxides may be used alone, or two or more kinds of organic peroxides may be used in combination.

The (C) basic filler of the present invention satisfies the following definitions from the viewpoint of the storage stability and the color tone stability. The (C) basic filler of the present invention refers a filler in which a dispersion of 1.0 g of the filler in a mixed solution of 40 g of distilled water and 10 g of ethanol has pH-value of 7.5 or more, preferably in the range from 7.5 to 9.0, more preferably in the range from 7.7 to 9.0, furthermore preferably in the range from 8.0 to 9.0, after stirring for 1 hour. A filler in which the dispersion has pH-value lower than 7.5 cannot suppress the deactivation of the aromatic amine compound, and the storage stability thereof tends to be low. On the other hand, since the hydrolysis and the like of the coexisting polymerizable monomer are accelerated, it is preferable that the pH value is 9.0 or less.

Specific examples of the filler usable as the (C) basic filler include silicate glass, more specifically, calcium silicate, aluminum silicate, fluoroalumino silicate glass, fluoroalumino borosilicate glass and other silicate glass. Among them, fluoroalumino silicate glass containing strontium and/or calcium ion and fluoroalumino borosilicate glass containing strontium and/or calcium ion are preferable. From the viewpoint of the storage stability, the composition range of the filler is preferably 15 to 35% by weight of $SiO_2$, 15 to 30% by weight of $Al_2O_3$, 20 to 45% by weight of SrO, 0 to 15% by weight of $P_2O_5$, 5 to 15% by weight of F, 0 to 10% by weight of $Na_2O$, 0 to 20% by weight of $B_2O_3$, and 0 to 10% by weight of CaO. Particularly preferable filler has the total content of $Al_2O_3$ and SrO within a range from 40 to 60% by weight in the above composition range. When the total content of $Al_2O_3$ and SrO is less than 40% by weight, the high basicity condition cannot be maintained and the color tone stability may be lowered. When the total content of $Al_2O_3$ and SrO is more than 60% by weight, the basicity of the filler may be excessive.

The above described (C) basic filler can be treated with a surface treatment material represented by a silane coupling material in order to improve the affinity to the polymerizable monomer, the dispersibility in the polymerizable monomer, and the mechanical strength and water resistance of the cured product, as long as the color tone stability and the storage stability are not impaired. The surface treatment material and the surface treatment method are not particularly limited, and known methods can be adopted without limitation. As a silane coupling agent used for surface treatment of the (C) basic filler, methyltrimethoxysilane, methyltriethoxysilane, methyltrichlorosilane, dimethyldichlorosilane, trimethylchlorosilane, vinyltrichlorosilane, vinyltriethoxysilane, vinyltris (6-methoxyethoxy) silane, γ-methacryloyloxypropyl trimethoxysilane, γ-chloropropyl trimethoxysilane, γ-glycidoxypropyl trimethoxysilane, hexamethyldisilazane and the like are preferable. In addition to the silane coupling material, surface treatment of the (C) basic filler can be performed by a method using a titanate coupling material or an aluminate coupling material. The treatment amount of the surface treatment material in the (C) basic filler is preferably 0.01 to 30 parts by weight, more preferably 0.5 to 20 parts by weight based on 100 parts by weight of the filler before treatment from the viewpoint of not reducing the basicity.

The shape of the (C) basic filler is not particularly limited, and amorphous and spherical fillers can be used. The average particle diameter of the (C) basic filler is preferably within a range from 0.01 μm to 50 μm, more preferably from 0.1 μm to 30 μm, still more preferably from 0.5 μm to 20 μm, and further still more preferably from 0.5 μm to 10 μm.

From the viewpoint of the color tone stability, the compounding amount of the (C) basic filler in the first paste is preferably within a range from 10 to 80 parts by weight, more preferably from 30 to 80 parts by weight, furthermore preferable from 50 to 80 parts by weight based on 100 parts by weight of the total amount of composition of the first paste.

In the present invention, from the viewpoint of the storage stability and the color tone stability, the compounding amount of the (C) basic filler in the second paste is within a range from 30 to 80 parts by weight, preferably from 40 to 80 parts by weight, more preferably from 50 to 80 parts by weight based on 100 parts by weight of total amount of the composition of the second paste.

Furthermore, from the viewpoint of the color tone stability, the total amount of the (C) basic filler in the first paste and the second paste is preferably within a range from 40 to 80 parts by weight, more preferably from 50 to 80 parts by weight based on 100 parts by weight total amount of the composition in which the first paste and the second paste are combined (or the two-paste type dental polymerizable composition). When the compounding amount of the basic filler is less than 40 parts by weight, the color tone stability may be poor, and when the compounding amount of the basic filler is more than 80 parts by weight, the paste property of the composition may become hard and handling may become difficult.

As the (C) basic filler, a basic filler satisfying the above definition may be used alone, or two or more kinds of basic fillers may be used in combination. Moreover, a non-basic filler may be compounded in the polymerizale composition of the present invention in the range in which as long as the color tone stability and storage stability are not impaired.

In the present invention, the non-basic filler refers a filler in which a dispersion has pH-value less than 7.5 based on the definition of the above-mentioned preferable basic filler, and inorganic compounds containing silica as the main component such as silica and silica-zirconia, and trifluororeutbium are included.

The non-basic filler can be treated with a surface treatment material represented by a silane coupling material in order to improve the affinity to the polymerizable monomer, the dispersibility in the polymerizable monomer, and the mechanical strength and water resistance of the cured product in the same manner as the (C) basic filler.

The shape of the non-basic filler is not particularly limited, and amorphous and spherical fillers can be used. Moreover, the average particle diameter of the non-basic filler is within a range from 0.01 μm to 50 μm.

Specific examples of the (D) aromatic amine compound as a chemical polymerization accelerator include 2,2-[3-(methylphenyl) imino] bisethanol acetate, 1,1-[(4-methylphenyl) imino] bis (2-propanol), p-tolyl diethanol amine, N,N-bis (2,2,2-trifluoroethyl)-p-toluidine, N,N-di (1-hydroxyethyl)-p-toluidine, N, N-di (2-hydroxypropyl)-p-toluidine, N-(1-cyanoethyl)-N-(1-acetoxyethyl)-m-toluidine, N,N-di (1-chloroethyl)-p-toluidine, N, N-dimethyl-p-toluidine, N-ethyl-N-methylaniline, N,N-dimethyl-aniline, N,N-dipropyl-o-toluidine, N,N-dipropyl-m-toluidine, N,N-dipropyl-p-toluidine and the like. Among these aromatic amine compounds, N,N-dimethyl-p-toluidine and N,N-di (1-hydroxyethyl)-p-toluidine are preferably used because of excellent solubility in polymerizable monomers and high reactivity with organic peroxides. The compounding amount of the (D) aromatic amine compound as a chemical polymerization accelerato is preferably 0.1 to 5 parts by weight, more preferably 0.3 to 3 parts by weight based on 100 parts by weight of the total amount of polymerizable monomer in the second paste. When the compounding amount of the aromatic amine compound is more than 5 parts by weight, there is a case in which the color tone stability decrease due to the remaining aromatic amine which does not contribute to the curing reaction. When the compounding amount of the aromatic amine compound is less than 0.1 parts by weight, there is a case in which sufficient curing acceleration effect may not be acquired.

As the compound as the (D) chemical polymerization accelerator, the above-mentioned aromatic amine compounds may be used alone, or two or more kinds of aromatic amine compounds may be used in combination.

In the polymerizable composition of the present invention, in order to further improve the curability, a polymerization accelerator other than the above-described aromatic amine compounds may be compounded. Examples of the other polymerization accelerators include aliphatic amine, sulfinic acid derivative, sulfur-containing reductive inorganic compound, nitrogen-containing reductive inorganic compound, borate compound, barbituric acid derivative, triazine compound, copper compound, tin compound, vanadium compound, halogen compound and the like.

Specific examples of aliphatic amine include primary aliphatic amines such as n-butylamine, n-hexylamine and n-octylamine; secondary aliphatic amines such as diisopropylamine and dibutylamine; tertiary aliphatic amines such as N-methyl diethanolamine, N-ethyl diethanolamine, N-n-butyl diethanolamine, N-lauryl diethanolamine, 2-(dimethylamino) ethyl (meth) acrylate, N-methyl diethanolamine di (meth) acrylate, N-ethyl diethanolamine di (meth) acrylate, triethanolamine mono (meth) acrylate, triethanolamine di (meth) acrylate, triethanolamine tri (meth) acrylate, triethanolamine, trimethylamine, triethylamine and tributylamine and the like. Among these, tertiary aliphatic amines are preferable from the viewpoint of the curability and storage stability of the composition, and among them, 2-(dimethyl amino) ethyl (meth) acrylate and N-methyl diethanolamine di (meth) acrylate are preferable.

Examples of sulfinic acid derivative include salts (alkali metals or alkaline earth metals are preferred) of p-toluenesulfinic acid, benzenesulfinic acid, 2,4,6-trimethyl benzenesulfinic acid, 2,4,6-triethyl benzenesulfinic acid, 2,4,6-triisopropyl benzenesulfinic acid and the like. Specific examples of salt compounds of these sulfinic acids include sodium p-toluenesulfinate and sodium benzenesulfinate.

Examples of sulfur-containing reductive inorganic compound include sulfites, bisulfites, pyrosulfites, thiosulfates, thionates and dithionite. Specific examples include sodium sulfite, potassium sulfite, calcium sulfite, ammonium sulfite, sodium bisulfite, potassium bisulfite and the like.

Examples of nitrogen-containing reductive inorganic compound include nitrites, and specific examples include sodium nitrite, potassium nitrite, calcium nitrite, ammonium nitrite and the like.

Specific examples of borate compound include trialkylphenylboron, trialkyl (p-chlorophenyl) boron, trialkyl (p-fluorophenyl) boron, trialkyl (3,5-bistrifluoro methyl) phenyl boron, trialkyl [3,5-bis (1,1,1,3,3,3-hexafluoro-2-methoxy-2-propyl) phenyl] boron, trialkyl (p-nitrophenyl) boron, trialkyl (m-nitrophenyl) boron, trialkyl (p-butylphenyl) boron, trialkyl (m-butylphenyl) boron, trialkyl (p-butyloxyphenyl) boron, trialkyl (m-butyloxyphenyl) boron, trialkyl (p-octyloxyphenyl) boron and trialkyl (m-octyloxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like).

Specific examples of barbituric acid derivative include salts (alkali metals or alkaline earth metals are preferred) of barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl barbituric acid, 1,3-dimethyl-5-cyclopentyl barbituric acid, 1,3-dimethyl-5-cyclohexyl barbituric acid 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids. Specifically, the salts of these barbituric acids include sodium 5-butyl barbiturate, sodium 1,3,5-trimethyl barbiturate, sodium 1-cyclohexyl-5-ethyl barbiturate and the like.

Specific examples of the triazine compound include 2,4,6-tris(trichloro methyl)-s-triazine, 2,4,6-tris(tribromo methyl)-s-triazine, 2-methyl-4,6-bis(trichloro methyl)-s-triazine, 2-methyl-4,6-bis(tribromo methyl)-s-triazine, 2-phenyl-4,6-bis(trichloro methyl)-s-triazine, 2-(p-methoxy phenyl)-4,6-bis(trichloro methyl)-s-triazine, 2-(p-methyl thiophenyl)-4,6-bis(trichloro methyl)-s-triazine, 2-(p-chloro phenyl)-4,6-bis(trichloro methyl)-s-triazine, 2-(2,4-dichloro phenyl)-4,6-bis(trichloro methyl)-s-triazine, 2-(p-bromo phenyl)-4,6-bis(trichloro methyl)-s-triazine, 2-(p-tolyl)-4,6-bis(trichloro methyl)-s-triazine, 2-n-propyl-4,6-bis(trichloro methyl)-s-triazine, 2-(α,α,β-trichloro ethyl)-4,6-bis (trichloro methyl)-s-triazine, 2-styryl-4,6-bis(trichloro methyl)-s-triazine, 2-[2-(p-methoxy phenyl) ethenyl]-4,6-bis(trichloro methyl)-s-triazine, 2-[2-(o-methoxy phenyl) ethenyl]-4,6-bis(trichloro methyl)-s-triazine, 2-[2-(p-butoxy phenyl) ethenyl]-4,6-bis(trichloro methyl)-s-triazine, 2-[2-(3,4-dimethoxy phenyl) ethenyl]-4,6-bis (trichloro methyl)-s-triazine, 2-[2-(3,4,5-trimethoxy phenyl) ethenyl]-4,6-bis (trichloro methyl)-s-triazine, 2-(1-naphthyl)-4,6-bis (trichloro methyl)-s-triazine, 2-(4-biphenylyl)-4,6-bis (trichloro methyl)-s-triazine, 2-[2-{N,N-bis(2-hydroxy ethyl) amino} ethoxy]-4,6-bis(trichloro methyl)-s-triazine, 2-[2-{N-hydroxy ethyl-N-ethylamino} ethoxy]-4,6-bis (trichloro methyl)-s-triazine, 2-[2-{N-hydroxy ethyl-N-methylamino} ethoxy]-4,6-bis(trichloro methyl)-s-triazine, 2-[2-{N, N-diallylamino} ethoxy]-4,6-bis(trichloro methyl)-s-triazine and the like.

Specific examples of the copper compound include copper acetylacetone, cupric acetate, copper oleate, cupric chloride, cupric bromide and the like.

Specific examples of tin compound include di-n-butyl tin dimaleate, di-n-octyl tin dimaleate, di-n-octyl tin dilaurate, di-n-butyl tin dilaurate and the like. Among them, the tin compound is preferably di-n-octyl tin dilaurate and di-n-butyl tin dilaurate.

Specific examples of vanadium compound include divanadium oxide (IV), vanadium oxide acetylacetonate (IV), vanadyl oxalate (IV), vanadyl sulfate (IV), oxobis (1-phenyl-1,3-butanedionate) vanadium (IV), bis (maltolate) oxovanadium (IV), vanadium pentoxide (V), sodium metavanadate (V), ammonium metavanadate (V) and the like.

Specific examples of the halogen compound include dilauryl dimethyl ammonium chloride, lauryl dimethyl benzyl ammonium chloride, benzyl trimethyl ammonium chloride, tetramethyl ammonium chloride, benzyl dimethyl acetyl ammonium chloride, dilauryl dimethyl ammonium bromide and the like.

A photopolymerization initiator may be compounded in the polymerizable composition of the present invention in order to impart photopolymerizability.

Specific examples of the photopolymerization initiator include α-diketones, mono-, bis-, or tris acylphosphine oxide compound and mono- or di-acylgermanium compound. The compounding amount of the photopolymerization initiator is not particularly limited, however from the viewpoint of photocurability, is preferably within a range from 0.01 to 5 parts by weight, more preferably from 0.10 to 3 parts by weight based on 100 parts by weight of total amount of the polymerizable monomer in the two-paste type dental polymerizable composition.

Specific examples of α-diketones include diacetyl, dibenzyl, camphorquinone, 2,3-pentadione, 2,3-octadione, 9,10-phenanthrenequinone, 4,4'-oxybenzyl, acenaphthenequinone and the like. Among these, camphor quinone is preferable because it is excellent in photocurability in the visible and near-ultraviolet regions and exhibits sufficient photocurability even if any light source of a halogen lamp, a light emitting diode (LED) and a xenon lamp are used.

Examples of mono-, bis-, or tris acylphosphine oxide compound include bis (2,6-dimethoxy benzoyl) phenyl phosphine oxide, bis (2,6-dimethoxy benzoyl) (2,4,4-trimethyl pentyl) phosphine oxide, bis (2,6-dimethoxy benzoyl)-n-butyl phosphine oxide, bis (2,6-dimethoxy benzoyl)-(2-methylprop-1-yl) phosphine oxide, bis (2,6-dimethoxy benzoyl)-(1-methylprop-1-yl) phosphine oxide, bis (2,6-dimethoxy benzoyl)-t-butyl phosphine oxide, bis (2,6-dimethoxy benzoyl) cyclohexyl phosphine oxide, bis (2,6-dimethoxy benzoyl) octyl phosphine oxide, bis (2-methoxy benzoyl) (2-methylprop-1-yl) phosphine oxide, bis (2-methoxy benzoyl) (1-methylprop-1-yl) phosphine oxide, bis (2,6-diethoxy benzoyl) (2-methylprop-1-yl) phosphine oxide, bis (2,6-diethoxy benzoyl) (1-methylprop-1-yl) phosphine oxide, bis (2,6-dibutoxy benzoyl) (2-methylprop-1-yl) phosphine oxide, bis (2,4-dimethoxy benzoyl) (2-methylprop-1-yl) phosphine oxide, bis (2,4,6-trimethyl benzoyl) phenyl phosphine oxide, 2,4,6-trimethyl benzoyl diphenyl phosphine oxide, bis (2,4,6-trimethyl benzoyl) (2,4-dipentoxy phenyl) phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, 2,6-dimethoxy benzoyl benzyl butyl phosphine oxide, 2,6-dimethoxy benzoyl benzyl octyl phosphine oxide, bis (2,4,6-trimethyl benzoyl) isobutyl phosphine oxide, 2,6-dimethoxy benzoyl-2,4,6-trimethyl benzoyl-n-butyl phosphine oxide and the like. Among these, from the viewpoint of photocurability, bis (2,6-dimethoxy benzoyl) (2,4,4-trimethyl pentyl) phosphine oxide and 2,4,6-trimethyl benzoyl diphenyl phosphine oxide are preferable.

Examples of mono- or di-acylgermanium compound include bisbenzoyl diethylgermanium, bisbenzoyl dimethylgermanium, bisbenzoyl dibutylgermanium, bis (4-methoxybenzoyl) dimethylgermanium and bis (4-methoxybenzoyl) diethylgermanium and (4-methoxybenzoyl) diethylgermanium and the like are mentioned.

The polymerizable composition of the present invention preferably contains substantially no water from the viewpoint of storage stability. When water is contained in the composition, not only the curability is lowered, but also the storage stability may be lowered because the polymerizable monomer, which is hydrophobic, and water induce layer separation. In the present invention, containing substantially no water means not only the condition that the composition does not contain water at all, but also the condition that the presence of an extremely small amount not affecting the above-described effects of the present invention is acceptable. Usually, the presence of 3 parts by weight or less, more preferably 1 part by weight or less based on 100 parts by weight of the total amount of polymerizable monomer in the two-paste type dental polymerizable composition is acceptable.

The polymerizable composition of the present invention preferably contains substantially no acidic group-containing compound other than the chemical polymerization initiator and the chemical polymerization accelerator from the viewpoint of the color tone stability. When acidic group-containing compound is contained in the composition, because it reacts with the (C) basic filler and the basicity of the whole composition decrease, there is a case in which the storage stability and the color stability may be reduced. Examples of the acidic group include acidic groups such as phosphoric acid group, pyrophosphoric acid group, thiophosphoric acid group, phosphonic acid group, sulfonic acid group, carboxylic acid group and the like. In the present invention, acidic group-containing compound refers a compound having at least one of these acid groups, and is not limited by the presence or absence of a polymerizable group. In the present invention, containing substantially no acidic group-containing compound means not only the condition that the composition does not contain acidic group-containing compound at all, but also the condition that the presence of an extremely small amount not affecting the above-described effects of the present invention is acceptable. Usually, the presence of 3 parts by weight or less, more preferably 1 part by weight or less based on 100 parts by weight of the total amount of polymerizable monomer in the two-paste type dental polymerizable composition is acceptable.

Moreover, the polymerizable composition of the present invention may be compounded with a well-known additives in the range in which as long as the properties does not decrease. Specific examples of such additives include polymerization inhibitors, antioxidants, pigments, dyes, ultraviolet absorbers, organic solvents, thickeners and the like.

Specific examples of the polymerization inhibitor include 2,6-di-butyl hydroxytoluene, hydroquinone, dibutyl hydroquinone, dibutyl hydroquinone monomethyl ether, 2,6-t-butylphenol and 2,6-di-t-butyl-4-methylphenol. The compounding amount of the polymerization inhibitor is preferably 0.001 to 1.0 parts by weight based on 100 parts by weight of the total amount of the polymerizable monomer in the two-paste type dental polymerizable composition.

EXAMPLES

Hereinafter, the present invention will be described in detail with reference to Examples and Comparative Examples. However, the present invention is not limited to these Examples. The abbreviations used below are as follows.

(A) Polymerizable Monomer
Bis-GMA: 2,2-bis [4-(3-(meth) acryloyloxy)-2-hydroxy propoxyphenyl] propane
UDMA: 2,2,4-trimethyl hexamethylene bis (2-carbamoyloxyethyl) dimethacrylate
2.6E: 2,2-bis (4-(meth) acryloyloxy polyethoxyphenyl) propane in which the average addition mole number of ethoxy groups is 2.6
TEGDMA: triethylene glycol dimethacrylate
NPG: neopentyl glycol dimethacrylate
2-HEMA: 2-hydroxyethyl methacrylate
TMPT: trimethylol propane tri (meth) acrylate
10-MDP: 10-methacryloyloxydecyl dihydrogen phosphate (polymerizable monomer having an acidic group)
(B) Polymerization Initiator
BPO: benzoyl peroxide
CHP: cumene hydroperoxide
(D) Polymerization accelerator
DMPT: N,N-dimethyl-p-toluidine
DEPT: N,N-di (1-hydroxyethyl)-p-toluidine
Others
CQ: camphorquinone
APO: 2,4,6-trimethyl benzoyl diphenyl phosphine oxide
pTNa: sodium p-toluenesulfinate
BHT: 2,6-di-t-butyl-4-methylphenol
Water: distilled water
(C): Filler
The preparing method of each filler is shown below.

The compositions (W/W %) of the raw material glasses GL1 to GL9 of the fillers are shown in the table.

TABLE 1

| | | \multicolumn{9}{c}{The composition of raw material glass} |
|---|---|---|---|---|---|---|---|---|---|---|
| | | GL1 | GL2 | GL3 | GL4 | GL5 | GL6 | GL7 | GL8 | GL9 |
| W/W (%) | $SiO_2$ | 32.2 | 24.2 | 27.3 | 23.7 | 62.2 | 40 | 75.3 | 45.6 | 30.2 |
| | $Al_2O_3$ | 19.3 | 22.6 | 24.2 | 19.4 | 12.5 | 28.2 | 10.2 | 10.9 | 35 |
| | SrO | 26.9 | 30.6 | 32.8 | 40.3 | 16.7 | 10.4 | 9.4 | 22.2 | 30.5 |
| | $P_2O_5$ | | | 5 | 2.8 | 2.4 | 9.5 | 1.5 | 5.8 | 1.3 |
| | F | 8.7 | 8.9 | 7.5 | 6.2 | 5.5 | 10.9 | 3.5 | 10.1 | 2.5 |
| | $Na_2O$ | 4 | 2.6 | 0.3 | | 0.7 | 1 | | 5.1 | 0.5 |
| | $B_2O_3$ | 8.9 | 11.1 | 2.9 | 1.8 | | | | | |
| | CaO | | | | 5.8 | | | | | |
| | Others | | | | | | | 0.1 | 0.3 | |
| | Total | 100.0 | 100.0 | 100.0 | 100.0 | 100.0 | 100.0 | 100.0 | 100.0 | 100.0 |
| | Average particle diameter (μm) | 8.5 | 0.4 | 2.4 | 4.5 | 1.5 | 0.9 | 0.7 | 3.5 | 2.2 |

The filler surface of the above-mentioned raw material glass was surface-treated by the treatment method shown below and used as a filler.

A silane coupling treatment solution prepared by stirring 100.0 g of water, 80.0 g of ethanol, 0.003 g of phosphoric acid, and 3.0 g of 3-methacryloyloxypropyl trimethoxysilane as a silane coupling agent at room temperature for 2 hours was added to 100.0 g of the raw material glass GL1 and stirred for 30 minutes. Thereafter, a heat treatment was performed at 140° C. for 15 hours to obtain a filler 1.

A silane coupling treatment solution prepared by stirring 100.0 g of water, 80.0 g of ethanol, 0.020 g of phosphoric acid, and 20.0 g of 3-methacryloyloxypropyl trimethoxysilane as a silane coupling agent at room temperature for 2 hours was added to 100.0 g of the raw material glass GL2 and stirred for 30 minutes. Thereafter, a heat treatment was performed at 140° C. for 15 hours to obtain a filler 2.

A silane coupling treatment solution prepared by stirring 100.0 g of water, 80.0 g of ethanol, 0.006 g of phosphoric acid, and 6.0 g of 3-methacryloyloxypropyl trimethoxysilane as a silane coupling agent at room temperature for 2 hours was added to 100.0 g of the raw material glass GL3 and stirred for 30 minutes. Thereafter, a heat treatment was performed at 140° C. for 15 hours to obtain a filler 3.

A silane coupling treatment solution prepared by stirring 100.0 g of water, 80.0 g of ethanol, 0.020 g of phosphoric acid, and 20.0 g of 3-methacryloyloxypropyl trimethoxysilane as a silane coupling agent at room temperature for 2 hours was added to 100.0 g of the raw material glass GL4 and stirred for 30 minutes. Thereafter, a heat treatment was performed at 140° C. for 15 hours to obtain a filler 4.

A silane coupling treatment solution prepared by stirring 100.0 g of water, 80.0 g of ethanol, 0.009 g of phosphoric acid, and 9.0 g of 3-methacryloyloxypropyl trimethoxysilane as a silane coupling agent at room temperature for 2 hours was added to 100.0 g of the raw material glass GL5 and stirred for 30 minutes. Thereafter, a heat treatment was performed at 140° C. for 15 hours to obtain a filler 5.

A silane coupling treatment solution prepared by stirring 100.0 g of water, 80.0 g of ethanol, 0.010 g of phosphoric acid, and 10.0 g of 3-methacryloyloxypropyl trimethoxysilane as a silane coupling agent at room temperature for 2 hours was added to 100.0 g of the raw material glass GL6 and stirred for 30 minutes. Thereafter, a heat treatment was performed at 140° C. for 15 hours to obtain a filler 6.

A silane coupling treatment solution prepared by stirring 100.0 g of water, 80.0 g of ethanol, 0.006 g of phosphoric acid, and 6.0 g of 3-methacryloyloxypropyl trimethoxysilane as a silane coupling agent at room temperature for 2 hours was added to 100.0 g of the raw material glass GL7 and stirred for 30 minutes. Thereafter, a heat treatment was performed at 140° C. for 15 hours to obtain a filler 7.

A silane coupling treatment solution prepared by stirring 100.0 g of water, 80.0 g of ethanol, 0.020 g of phosphoric acid, and 20.0 g of 3-methacryloyloxypropyl trimethoxysilane as a silane coupling agent at room temperature for 2 hours was added to 100.0 g of the raw material glass GL8 and stirred for 30 minutes. Thereafter, a heat treatment was performed at 140° C. for 15 hours to obtain a filler 8.

A silane coupling treatment solution prepared by stirring 100.0 g of water, 80.0 g of ethanol, 0.010 g of phosphoric acid, and 10.0 g of 3-methacryloyloxypropyl trimethoxysilane as a silane coupling agent at room temperature for 2 hours was added to 100.0 g of the raw material glass GL9 and stirred for 30 minutes. Thereafter, a heat treatment was performed at 140° C. for 15 hours to obtain a filler 9.

A silane coupling treatment solution prepared by stirring 100.0 g of water, 80.0 g of ethanol, and 6.0 g of 3-aminopropyl trimethoxysilane as a silane coupling agent at room temperature for 2 hours was added to 100.0 g of the raw material glass GL7 and stirred for 30 minutes. Thereafter, a heat treatment was performed at 140° C. for 15 hours to obtain a filler 10.

pH Measurement

The pH-value of a dispersion of 1.0 g of the filler in a mixed solution of 40 g of distilled water and 10 g of ethanol after stirring for 1 hour was measured. A filler having pH-value of 7.5 or more corresponds to the (C) basic filler of the present invention. A filler having pH-value less than 7.5 does not correspond to the (C) basic filler of the present invention, and is expressed as "non-basic filler" in Table 2. In addition, a filler having pH-value more than 9.0 is expressed as "high (C) basic filler." In Table 2.

TABLE 2

List of Filler

|  | Filler 1 | Filler 2 | Filler 3 | Filler 4 | Filler 5 | Filler 6 | Filler 7 | Filler 8 | Filler 9 | Filler 10 |
|---|---|---|---|---|---|---|---|---|---|---|
| Raw material glass | GL1 | GL2 | GL3 | GL4 | GL5 | GL6 | GL7 | GL8 | GL9 | GL7 |
| Average particle diameter | 8.5 | 0.5 | 2.5 | 4.6 | 1.6 | 1.1 | 0.9 | 3.5 | 2.2 | 0.9 |
| pH Measurement | 7.74 | 8.04 | 8.91 | 8.78 | 6.95 | 7.33 | 6.87 | 6.55 | 9.56 | 7.02 |
| Class | (C) basic filler | | | | non-basic filler | | | | high (C) basic filler | non-basic filler |

Preparing Method of Paste

Each material for the first paste or the second paste shown in Table 3 was mixed for 24 hours at 100 rpm condition using mix rotor VMRC-5 to prepare a resin liquid in which each material is dissolved. Thereafter, the resin liquid and filler were put into a kneading vessel, and were kneaded for 20 minutes at 1400 rpm using a rotation and revolution mixer ARV-300 to prepare a first paste and a second paste. Prepared first paste and second paste were filled into the double syringe of 5 mL manufactured by Mixpack (volume ratio of first paste to second paste is 1:1) to prepare Compositions 1 to 27 as a two-paste type dental polymerizable composition. In Examples and Comparative Examples, the first paste in the present invention is replaced with Paste A, and the second paste is replaced with Paste B.

| | | (A) polemerizable monomer | | | | | | | | (B) organic peroxide | | (D) chemical polymerization accelerator | | Others | |
|---|---|---|---|---|---|---|---|---|---|---|---|---|---|---|---|
| | | Bis-GMA | UDMA | 2.6E | TEGDMA | NPG | 2-HEMA | TMPT | 10-MDP | BPO | CHP | DMPT | DEPT | CQ | APO |
| Composition 1 | A | 50 | | | 50 | | | | | 1.8 | | | | 0.5 | |
| | B | 50 | | | 50 | | | | | | | | 1.3 | | |
| Composition 2 | A | | 20 | 40 | 30 | 10 | | | | 1.3 | | | | | 1.5 |
| | B | | 20 | 40 | 30 | 10 | | | | | | | 1.1 | | |
| Composition 3 | A | 30 | 30 | 10 | 15 | | | 15 | | 0.8 | | | | 0.5 | |
| | B | 30 | 30 | 10 | 15 | | | 15 | | | | | 0.6 | | |
| Composition 4 | A | | | 60 | 30 | | 10 | | | 1.1 | | | | 0.5 | |
| | B | | | 60 | 30 | | 10 | | | | | | 1 | | |
| Composition 5 | A | | 20 | 40 | 30 | 10 | | | | 1.3 | | | | | 1.5 |
| | B | | 20 | 40 | 30 | 10 | | | | | | | 0.9 | | |
| Composition 6 | A | | | 60 | 30 | | 10 | | | 1.3 | | | | 0.5 | |
| | B | | | 60 | 30 | | 10 | | | | | | 1.1 | | |
| Composition 7 | A | 25 | 25 | 10 | 40 | | | | | 1.3 | | | | 0.5 | |
| | B | 25 | 25 | 10 | 40 | | | | | | | | 1.1 | | |
| Composition 8 | A | | 20 | 40 | 30 | 10 | | | | 0.8 | | | | | 1.5 |
| | B | | 20 | 40 | 30 | 10 | | | | | | | 0.5 | | |
| Composition 9 | A | 30 | 30 | 10 | 15 | | | 15 | | 0.8 | | | | 0.5 | |
| | B | 30 | 30 | 10 | 15 | | | 15 | | | | | 0.6 | | |
| Composition 10 | A | | | 60 | 30 | | 10 | | | 1.1 | | | | 0.5 | |
| | B | | | 60 | 30 | | 10 | | | | | | 1 | | |
| Composition 11 | A | | 20 | 40 | 30 | 10 | | | | 1.3 | | | | | 1.5 |
| | B | | 20 | 40 | 30 | 10 | | | | | | | 0.9 | | |
| Composition 12 | A | | | 60 | 30 | | 10 | | | 1.3 | | | | 0.5 | |
| | B | | | 60 | 30 | | 10 | | | | | | 1.1 | | |
| Composition 13 | A | | 20 | 40 | 30 | 10 | | | | 1.3 | | | | | 1.5 |
| | B | | 20 | 40 | 30 | 10 | | | | | | | 1.1 | | |
| Composition 14 | A | 50 | | | 50 | | | | | 1.8 | | | | 0.5 | |
| | B | 50 | | | 50 | | | | | | | | 1.3 | | |
| Composition 15 | A | 25 | 25 | 10 | 40 | | | | | 1.3 | | | | 0.5 | |
| | B | 25 | 25 | 10 | 40 | | | | | | | | 1.1 | | |
| Composition 16 | A | | 20 | 40 | 30 | 10 | | | | 0.95 | | | | | 1.5 |
| | B | | 20 | 40 | 30 | 10 | | | | | | | 0.8 | | |
| Composition 17 | A | | 20 | 40 | 30 | 10 | | | | 1.3 | | | | | 1.5 |
| | B | | 20 | 40 | 30 | 10 | | | | | | | 1.1 | | |
| Composition 18 | A | | 20 | 40 | 30 | 10 | | | | 1.3 | | | | | 1.5 |
| | B | | 20 | 40 | 30 | 10 | | | | | | | 1.1 | | |
| Composition 19 | A | | 20 | 40 | 30 | 10 | | | | 1.3 | | | | | 1.5 |
| | B | | 20 | 40 | 30 | 10 | | | | | | | 1.1 | | |
| Composition 20 | A | | 30 | 30 | 10 | 25 | | | 5 | 1.1 | | | | 0.8 | |
| | B | | 30 | 30 | 10 | 25 | | | 5 | | | | 0.8 | | |
| Composition 21 | A | 50 | | | 50 | | | | | 3 | | | | 0.5 | |
| | B | 50 | | | 50 | | | | | | | | 1.3 | | |

-continued

| | | | | | | | | | | | |
|---|---|---|---|---|---|---|---|---|---|---|---|
| Composition 22 | A | 50 | | 50 | | | 5 | | | 1.3 | 0.5 |
| | B | 50 | | 50 | | | | | | 1.3 | |
| Composition 23 | A | 50 | | 50 | | | 1.2 | | | | 0.5 |
| | B | 50 | | 50 | | | | | | 2.2 | |
| Composition 24 | A | 50 | | 50 | | | 1.8 | | | | 0.5 |
| | B | 50 | | 50 | | | | | | 4.5 | |
| Composition 25 | A | 50 | | 30 | | 20 | 1.2 | | | | |
| | B | 50 | | 30 | | 20 | | | | 0.9 | |
| Composition 26 | A | 60 | | 20 | 20 | | 0.7 | | | | 0.5 |
| | B | 60 | | 20 | 20 | | | | | 0.6 | |
| Composition 27 | A | 40 | 20 | 40 | | | 1.5 | | | | 0.5 |
| | B | 40 | 20 | 40 | | | | | 0.4 | 0.4 | |
| Composition 28 | A | 30 | | 30 | 20 | 20 | 1.2 | | | | 0.5 |
| | B | 30 | | 30 | 20 | 20 | | | 0.2 | 0.7 | |
| Composition 29 | A | 30 | | 30 | 20 | 20 | 0.6 | 0.4 | | | 0.5 |
| | B | 30 | | 30 | 20 | 20 | | | | 0.9 | |
| Composition 30 | A | 30 | | 30 | 20 | 20 | 0.6 | 0.4 | | | 0.5 |
| | B | 30 | | 30 | 20 | 20 | | | | 0.9 | |

| | | Others | | | (C) filler | | | | | | | | | |
|---|---|---|---|---|---|---|---|---|---|---|---|---|---|---|
| | | p-TSNa | BHT | Water | Filler 1 | Filler 2 | Filler 3 | Filler 4 | Filler 5 | Filler 6 | Filler 7 | Filler 8 | Filler 9 | Filler 10 |
| Composition 1 | A | | 0.05 | | 300 | | | | | | | | | |
| | B | | | | 300 | | | | | | | | | |
| Composition 2 | A | | 0.05 | | | 230 | | | | | | | | |
| | B | | | | | 230 | | | | | | | | |
| Composition 3 | A | | 0.05 | | | | 200 | | 75 | | | | | |
| | B | | | | | | 200 | | 75 | | | | | |
| Composition 4 | A | | 0.05 | | | | | 290 | | | | | | |
| | B | | | | | | | 290 | | | | | | |
| Composition 5 | A | | 0.05 | | 180 | | | 120 | | | | | | |
| | B | | | | 180 | | | 120 | | | | | | |
| Composition 6 | A | | 0.05 | | | 175 | | 125 | | | | | | |
| | B | | | | | 175 | | 125 | | | | | | |
| Composition 7 | A | | 0.05 | | | | 200 | | | | 50 | | | |
| | B | | | | | | 200 | | | | 50 | | | |
| Composition 8 | A | | 0.05 | | | 100 | | | | 150 | | | | |
| | B | 0.3 | | | | 250 | | | | | | | | |
| Composition 9 | A | | 0.05 | | | | 200 | | 50 | | | | | |
| | B | | | | | | 200 | | 50 | | | | | |
| Composition 10 | A | | 0.05 | | | | | 200 | | | | 50 | | |
| | B | | | | | | | 200 | | | | 50 | | |
| Composition 11 | A | | 0.05 | | 180 | | | 70 | | 50 | | | | |
| | B | | | | 180 | | | 70 | | 50 | | | | |
| Composition 12 | A | | 0.05 | | | | | 150 | 50 | | | | | |
| | B | 0.1 | | | | | | 150 | 50 | | | | | |
| Composition 13 | A | | 0.05 | | | 150 | | | | | | 150 | | |
| | B | | | | | 150 | | | | | | 150 | | |
| Composition 14 | A | | 0.05 | | | 50 | | | | 200 | | | | |
| | B | | | | 200 | | | | | 50 | | | | |
| Composition 15 | A | | 0.05 | | | | 75 | | | | 200 | | | |
| | B | | | | | | 75 | | | | 200 | | | |
| Composition 16 | A | | 0.05 | | | 50 | | | | 250 | | | | |
| | B | 0.5 | | | | 50 | | | | 250 | | | | |
| Composition 17 | A | | 0.05 | | | | | | | | | | | 300 |
| | B | | | | | | | | | | | | | 300 |
| Composition 18 | A | | 0.05 | | | | | | | | | 320 | | |
| | B | | | | | | | | | | | 320 | | |
| Composition 19 | A | | 0.05 | | | | | | | | | | 280 | |
| | B | | | | | | | | | | | | 280 | |
| Composition 20 | A | | 0.05 | | 300 | | | | | | | | | |
| | B | | | | 300 | | | | | | | | | |
| Composition 21 | A | | 0.05 | | 250 | | | | | | | | | |
| | B | | | | 250 | | | | | | | | | |
| Composition 22 | A | | 0.05 | | 250 | | | | | | | | | |
| | B | | | | 250 | | | | | | | | | |
| Composition 23 | A | | 0.05 | | 250 | | | | | | | | | |
| | B | | | | 250 | | | | | | | | | |
| Composition 24 | A | | 0.05 | | 250 | | | | | | | | | |
| | B | | | | 250 | | | | | | | | | |
| Composition 25 | A | | 0.05 | 1.5 | | 150 | 120 | | | | | | | |
| | B | | | 1.5 | | 150 | 120 | | | | | | | |
| Composition 26 | A | | 0.05 | | 80 | 80 | 70 | | | | | | | |
| | B | 0.4 | | | 80 | 80 | 70 | | | | | | | |
| Composition 27 | A | | 0.05 | | 80 | 80 | 70 | | | | | | | |
| | B | | | | 80 | 80 | 70 | | | | | | | |
| Composition 28 | A | | 0.05 | | 250 | | | | | | | | | |
| | B | 0.5 | | | 250 | | | | | | | | | |

| | | -continued | | |
|---|---|---|---|---|
| Composition 29 | A | 0.05 | | 230 |
| | B | | | 230 |
| Composition 30 | A | 0.05 | | 450 |
| | B | | | 450 |

The test method of each characteristic evaluated in the example and the comparative example is as follows. Each test was carried out under the conditions of automatic mixing with the mixing tip attached.

Curing Time Measurement

Curing time of the kneaded material of the pastes A and B was measured according to ISO 4049: 2009 (E). Specifically, 0.8 g of the kneaded paste was filled in a sample (4 mm φ×6 mm: manufactured by Teflon) attached with a thermocouple, and an exothermic curve due to a curing reaction is recorded. The time from the start of kneading of the paste to the peak of the exothermic curve was taken as the curing time, and the three measurements were averaged.

Storage Stability

The above described curing time immediately after preparation of the paste was compared with that after storage at 40° C. for 5 months. The rating criteria were as follow: ○: The delay rate was less than 120%; Δ: The delay rate was 120% or more and less than 140%; and x: The delay rate was 140% or more.

Delay rate (%)=(curing time after storage at 40° C. for 5 months)/(curing time immediately after preparation)×100

Color Tone Stability

A stainless mold (15φ×1 mm: disk shape) was filled with a kneaded material of the Paste A and Paste B which are stored at 40° C. for 5 months, and cover glass was placed on upper side of the stainless mold to apply pressure with glass plate. Thereafter, light irradiatdion was performed on the both sides for 3 minutes using a photopolymerization irradiator (Solidelite V manufactured by Shofu Inc.) via the cover glass to prepare a cured material and the cured material was taken out of the mold and was used as a test body. These test bodies were immersed in water at 70° C. for one month. The rating criteria were as follow: ○: The color difference ΔE between before and after the immersion was less than 2; Δ: The color difference ΔE between before and after the immersion was 2 or more and less than 5; and x: The color difference ΔE between before and after the immersion was 5 or more.

Paste Properties and Operability

Pastes immediately after preparation and after storing at 40° C. for 5 months were visually observed and evaluated in the following rating criteria.

○: No changes of paste properties were observed in the pastes immediately after preparation and after storing at 40° C. for 5 months E: In the paste after storing at 40° C. for 5 months, slight separation was observed.

G: In the paste after storing at 40° C. for 5 months, slight gelation was observed.

Δ: Curing of the paste was fast to cause inconvenience in handling.

x: The paste property immediately after preparation was hard and handling was difficult.

The tests described above were performed on compositions 1 to 27, and the results are shown in Table 4. The compositions 1-14 and 20-29 which satisfy the storage stability and the color tone stability were described as Examples 1-25, respectively.

TABLE 4

| | | Curing time (sec) | | Storage stability | | |
|---|---|---|---|---|---|---|
| | | Immediately after preparation | 40° C. 5 months | Delay rate (%) | Color tone stability | Paste Properties |
| Example 1 | Composition 1 | 182 | 201 | 110 | ○ | ○ | ○ |
| Example 2 | Composition 2 | 245 | 248 | 101 | ○ | ○ | ○ |
| Example 3 | Composition 3 | 338 | 342 | 101 | ○ | ○ | ○ |
| Example 4 | Composition 4 | 302 | 305 | 101 | ○ | ○ | ○ |
| Example 5 | Composition 5 | 253 | 269 | 106 | ○ | ○ | ○ |
| Example 6 | Composition 6 | 250 | 275 | 110 | ○ | ○ | ○ |
| Example 7 | Composition 7 | 246 | 248 | 101 | ○ | ○ | ○ |
| Example 8 | Composition 8 | 222 | 240 | 108 | ○ | Δ | ○ |
| Example 9 | Composition 9 | 296 | 325 | 110 | ○ | ○ | ○ |
| Example 10 | Composition 10 | 239 | 269 | 113 | ○ | ○ | ○ |
| Example 11 | Composition 11 | 220 | 241 | 110 | ○ | ○ | ○ |
| Example 12 | Composition 12 | 195 | 222 | 114 | ○ | Δ | ○ |
| Example 13 | Composition 13 | 220 | 300 | 136 | Δ | Δ | ○ |
| Example 14 | Composition 14 | 174 | 189 | 109 | ○ | Δ | ○ |
| Comparative Example 1 | Composition 15 | 243 | 432 | 178 | x | x | ○ |
| Comparative Example 2 | Composition 16 | 207 | 268 | 129 | Δ | x | ○ |
| Comparative Example 3 | Composition 17 | 243 | 424 | 174 | x | x | ○ |
| Comparative Example 4 | Composition 18 | 238 | 544 | 229 | x | x | ○ |
| Example 15 | Composition 19 | 209 | 282 | 135 | Δ | Δ | ○ |
| Example 16 | Composition 20 | 319 | 433 | 135 | Δ | Δ | G |

TABLE 4-continued

| | | Storage stability | | | | |
|---|---|---|---|---|---|---|
| | | Curing time (sec) | | | | |
| | | Immediately after preparation | 40° C. 5 months | Delay rate (%) | Color tone stability | Paste Properties |
| Example 17 | Composition 21 | 120 | 155 | 129 | Δ | Δ | Δ |
| Example 18 | Composition 22 | 89 | 122 | 137 | Δ | Δ | G · Δ |
| Example 19 | Composition 23 | 175 | 192 | 110 | ○ | Δ | ○ |
| Example 20 | Composition 24 | 88 | 92 | 105 | ○ | Δ | Δ |
| Example 21 | Composition 25 | 234 | 275 | 118 | ○ | Δ | E |
| Example 22 | Composition 26 | 204 | 232 | 114 | ○ | ○ | ○ |
| Example 23 | Composition 27 | 180 | 185 | 103 | ○ | ○ | ○ |
| Example 24 | Composition 28 | 171 | 208 | 122 | ○ | ○ | ○ |
| Example 25 | Composition 29 | 185 | 209 | 113 | ○ | ○ | ○ |
| Comparative Example 5 | Composition 30 | 200 | 208 | 104 | ○ | ○ | x |

In Examples 1 to 25 in which each component satisfies the constitution of the present invention, no delay of curing time of 140% or more was observed even after storage for 5 months at 40° C., and high storage stability was observed. Furthermore, the large color tone change of the cured material was hardly recognized, and therefore it can fully endure the use as a dental composition mounted in an oral cavity for a long time. In Examples 1 to 25, in comparison with the pastes immediately after preparation and after storage for 5 months at 40° C., although gelation, separation, and short curing time were recognized in some pastes after storage for 5 months at 40° C., it was confirmed that there was no significant difference in paste properties in operation. In addition, the curing time of these dental compositions can be arbitrarily adjusted by adding a plurality of polymerization accelerators or increasing or decreasing the compounding amount thereof, and it is possible to use as a two-paste type dental polymerizable composition such as dental resin cement and dental abutment construction material.

In Comparative Examples 1 to 4, it was confirmed that the curing time was delayed and the color stability was low. Although Comparative Examples 1 and 2 partially contain the basic filler, the filling amount is less than 40 parts by weight based on 100 parts by weight of total amount of the composition of the first paste and the second paste, and Comparative Examples 3 and 4 do not contain a basic filler, therefore it is predicted that the aromatic amine becomes unstable and deactivates. Moreover, although the comparative example 3 contains the filler 10 treated by using 3-aminopropyl trimethoxysilane which has basicity as a filler, since the basicity as a filler is not enough, it was recognized that storage stability decreases.

It was confirmed that although Comparative Example 5 had high color tone stability and storage stability, the filler filling rate was high and therefore the paste property was hard and the handling was difficult.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

The present invention has been widely used in the dental field, as a dental resin cement, a dental abutment construction material, a dental adhesive material, a dental coating material, a pit and fissure plugging material, a composite resin, a dental autopolymerizing resin, a dental pretreatment material, a denture base material and the like, and thereofore can be industrially applied.

What is claimed is:

1. A two-paste type dental polymerizable composition comprising:
   a first paste containing (A) at least one polymerizable monomer, an (B) organic peroxide as a chemical polymerization initiator, and a (C) basic filler, and
   a second paste containing (A) at least one polymerizable monomer, a (C) basic filler and an (D) aromatic amine compound as a chemical polymerization accelerator, wherein
   the second paste contains 30 to 80 parts by weight of the (C) basic filler based on 100 parts by weight of the total amount of the second paste,
   a dispersion of 1.0 g of the (C) basic filler in a mixed solution of 40 g of distilled water and 10 g of ethanol has a pH-value in the range from 7.5 to 9.0 after stirring for 1 hour, and
   the first paste and the second paste contain no acidic group-containing compound.

2. The two-paste type dental polymerizable composition according to claim 1, wherein:
   the total compounding amount of the (C) basic filler contained in the first paste and the second paste is in the range from 40 to 80 parts by weight based on 100 parts by weight of the total composition of the first paste and the second paste.

3. The two-paste type dental polymerizable composition according to claim 1, wherein:
   the first paste and the second paste contain substantially no water.

4. The two-paste type dental polymerizable composition according to claim 1, wherein:
   a volume mixing ratio of the first paste to the second paste is in the range from 1:0.9 to 0.9:1.

5. The two-paste type dental polymerizable composition according to claim 2, wherein:
   the first paste and the second paste contain substantially no water.

6. The two-paste type dental polymerizable composition according to claim 2, wherein:

a volume mixing ratio of the first paste to the second paste is in the range from 1:0.9 to 0.9:1.

7. The two-paste type dental polymerizable composition according to claim 3, wherein:
a volume mixing ratio of the first paste to the second paste is in the range from 1:0.9 to 0.9:1.

* * * * *